United States Patent [19]
Grace et al.

[11] Patent Number: 5,338,366
[45] Date of Patent: Aug. 16, 1994

[54] ACID PRE-HYDROLYSIS REACTOR SYSTEM

[75] Inventors: Todd S. Grace; Mark D. Barrett; Vic L. Bilodeau; Gary L. McCarty; Brian F. Greenwood; J. Robert Prough; Louis O. Torregrossa, all of Glens Falls, N.Y.

[73] Assignee: Kamyr, Inc., Glens Falls, N.Y.

[21] Appl. No.: 997,711

[22] Filed: Jan. 4, 1993

[51] Int. Cl.$^5$ .................. C13D 1/14; D21B 1/12
[52] U.S. Cl. ............................ 127/37; 127/1; 127/44; 162/14; 162/23
[58] Field of Search ............. 127/1, 37, 44; 162/14, 162/23

[56] References Cited

U.S. PATENT DOCUMENTS

| | | | |
|---|---|---|---|
| 2,086,701 | 7/1937 | Dreyfus | 127/37 |
| 2,752,270 | 6/1956 | Specht | 127/37 |
| 3,067,065 | 12/1962 | Kusama | 127/37 |
| 3,523,911 | 8/1970 | Funk et al. | 127/37 |
| 4,023,982 | 5/1977 | Knauth | 127/37 |
| 4,168,988 | 9/1979 | Riehm et al. | 127/37 |
| 4,237,226 | 12/1980 | Grethlein | 127/37 |
| 4,427,453 | 1/1984 | Reitter | 127/37 |
| 4,436,586 | 3/1984 | Elmore | 162/19 |
| 4,556,430 | 12/1985 | Converse et al. | 127/36 |
| 4,612,286 | 9/1986 | Sherman et al. | 435/157 |
| 4,668,340 | 5/1987 | Sherman | 162/16 |
| 4,968,385 | 11/1990 | Amador et al. | 162/18 |
| 5,221,357 | 6/1993 | Brink | 127/43 |

OTHER PUBLICATIONS

Lambert et al, "Economic Evaluation of TVA's Dilute Acid Process . . . Hardwoods", Tennessee Valley Authority, Mar. 1989.

Primary Examiner—Paul Lieberman
Assistant Examiner—Patricia L. Hailey
Attorney, Agent, or Firm—Nixon & Vanderhye

[57] ABSTRACT

Biomass, such as bagasse, is pre-hydrolyzed, to ultimately effect hydrolysis of hemicellulose to sugars. Biomass is mixed with a mineral acid solution to form a slurry having a consistency of about 8 to 12% so that the acid solution properly wets the biomass. Then the slurry is dewatered to about 35 to 50% consistency, and is heated to reaction temperature (e. g. about 320° F.) by direct contact with steam in the vapor phase of a vertical pressurized reactor, having a pressure of about 40 psig. A fluffer is preferably provided in the top of the reaction vessel. After a reaction time of about 30 minutes, the biomass is diluted and cold blown out of the bottom of the reactor. Pressate from the dewatering has acid added to it and is heated by indirect heat exchange with a sugar solution obtained by washing of the biomass discharged from the reactor, and is then mixed with the biomass as the acid solution.

29 Claims, 2 Drawing Sheets

ACID PRE-HYDROLYSIS REACTOR SYSTEM

BACKGROUND AND SUMMARY OF THE INVENTION

There are many geographic locations around the world where it is highly desirable to hydrolyze hemicellulose and cellulose in biomass, particularly waste cellulose containing products. For example it is highly desirable to be able to hydrolyze the hemicellulose and cellulose in agricultural wastes (such as bagasse), waste paper, and cellulose-containing municipal solid wastes.

In general, biomass contains cellulose, hemicellulose, lignin and ash. When the biomass is treated with hot dilute mineral acid the hemicellulose and cellulose will be hydrolyzed. The hemicellulose is typically converted to primary five carbon sugars, while the cellulose is converted to primary six carbon sugars. The soluble sugars can be separated from the lignin solids by conventional means, leaving a sugar solution. The sugar solution can be fermented into ethanol, which—after purification—has many end uses, including as a fuel additive. Exemplary procedures and apparatus for alcohol production from biomass are disclosed in U.S. Pat. Nos. 4,436,586 and 4,612,286.

One particularly desirable step in the production of ethanol from biomass is pre-hydrolysis. Pre-hydrolysis comprises the hydrolyzing of hemicellulose to sugars (while the cellulose is not hydrolyzed). In addition to hydrolyzing the hemicellulose, pre-hydrolysis swells the cellulose, which enhances the effectiveness of subsequent hydrolysis of the cellulose to simple sugars.

According to the present invention a method and apparatus are provided for acid pre-hydrolysis of biomass. The invention provides a simple yet effective manner for practicing pre-hydrolysis. The method and apparatus according to the invention may be used as a preliminary to a wide variety of other techniques for acting on the biomass being treated, or the hydrolysate produced, such as hydrolyzing of the cellulose, production of paper pulp, production of alcohol and furfural, and the like.

According to one aspect of the present invention a method of acid pre-hydrolysis of biomass, effecting hydrolysis of hemicellulose to sugars, is provided. The invention comprises the steps of automatically, continuously, and sequentially: (a) Mixing biomass containing hemicellulose with a mineral acid solution of sufficient concentration to eventually hydrolyze the hemicellulose therein, and to form a slurry having a consistency that insures proper wetting of the biomass with mineral acid. (b) Dewatering the slurry so as to minimize the amount of steam required to heat the biomass to reaction temperature and to maintain a desired sugar solution concentration after prehydrolysis. (c) Heating the dewatered slurry to reaction temperature, at superatmospheric pressure by direct contact with steam. And, (d) retaining the biomass in the dewatered slurry at reaction temperature and pressure conditions for a time sufficient to hydrolyze the hemicellulose of the biomass.

Step (a) can be practiced using biomass such as agricultural wastes (bagasse), waste paper, and municipal solid cellulose waste. Step (a) is also practiced to form a slurry having a consistency of about 8 to 12%, while step (b) is practiced to dewater the slurry to a consistency of about 35 to 50%. During the practice of step (b) a pressate is produced, and the invention also comprises the steps: (e) Adding mineral acid to the pressate to form a mixture of pressate and acid. (f) Heating the mixture of pressate and acid. And (g), using the heated mixture as the acid solution source in step (a). Step (f) is practiced by (g) washing the biomass from step (d) to produce a sugar solution having a temperature well above 100° F., and (h) passing the sugar solution into indirect, heat exchange, contact with the mixture of pressate and acid. Also there preferably is the further step between steps (b) and (c) of fluffing the dewatered slurry. The amount of acid solution added in step (a) is also typically automatically controlled in response to the mass flow rate of biomass used in step (a).

In the typical practice of the method of the invention, steps (c) and (d) are practiced in a pressurized vertical reactor, and step (c) takes place in a vapor phase at the top of the reactor, and comprises the further steps of diluting and cold blowing the biomass from the bottom of the reactor. Steps (c) and (d) are practiced at a pressure which typically is about 30 to 50 psig (e.g. about 40 psig), at a temperature of about 250°–350° F. (e.g. about 320° F.), and for a time of about 20 to 40 minutes (e.g. about 30 minutes). Step (b) may be practiced in a dewatering press, and there preferably is the further step of preventing vapors from the top of the reactor from passing back to the dewatering press. The consistency of the biomass slurry at the top of the reactor is typically about 34%, and 24% at the bottom, and the diluting step is practiced to dilute the biomass to a consistency of about 8 to 12%. Cold blowing takes place at a temperature of about 180° F.

According to another aspect of the present invention a method of acid pre-hydrolysis of biomass, effecting hydrolysis of hemicellulose to sugars, comprises the automatic, continuous, and sequential practice of the following steps: (a) Mixing biomass containing hemicellulose with a mineral acid solution of about 0.5–3.0% (typically about 1%) to form a slurry having a consistency of about 8–12%. (b) Dewatering the slurry to a consistency of about 35–50%. (c) Heating the dewatered slurry to a temperature of about 250°–350° F., at a pressure of about 30–50 psig, by direct contact with steam. And, (d) retaining the biomass in the dewatered slurry at reaction temperature and pressure conditions for a time sufficient to hydrolyze the hemicellulose of the biomass.

According to yet another aspect of the present invention, a pre-hydrolysis reactor system is provided. The reactor system comprises the following elements: A mixer having a first inlet for substantially dry biomass, and a second inlet for acid solution, and an outlet for slurried biomass. An impregnation press having an inlet connected to the outlet from the mixer, a dewatered biomass outlet, and a pressate outlet. A vertical reactor having a top and a bottom, and first and second inlets at the top thereof for biomass slurry and steam, respectively, arranged to provide a vapor phase at the top of the reactor. High density feed means connected between the impregnation press biomass outlet and the reactor first inlet for feeding high density biomass into the vertical reactor first inlet. And, a cold blow prehydrolyzed biomass outlet from the bottom of the reactor. A fluffer is preferably disposed in the top of the reactor between the first and second inlets, the second inlet being vertically above the first inlet.

The reactor system also may comprise the following further additional elements: A pressate tank having an inlet and an outlet. A pressate line extending from the impregnation press pressate outlet to the pressate tank inlet. An indirect heat exchanger. A pump. A transport line interconnecting the pressate tank outlet, pump and heat exchanger so that pressate is pumped from the tank through the heat exchanger. An acid addition line connected to the transport line between the pressate tank and the pump. And, a discharge line from the heat exchanger connected to the second inlet to the mixer. A weigh conveyor may be operatively connected to the mixer first inlet, and a flow control valve disposed in the discharge line from the heat exchanger. A controller is provided for controlling the flow control valve in response to the weigh conveyor.

Typically the mixer is disposed vertically above the impregnation press, and the inlet to the impregnation press and the outlet from the mixer are connected by a feed chute. The impregnation press is vertically above the high pressure feed means (which may comprise a high density feed pump), and the impregnation press biomass outlet is connected to the high pressure feed means inlet by a chute. The high pressure feed means also comprises means for preventing passage of vapors from the reactor back to the impregnation press.

It is the primary object of the present invention to provide a simple yet effective method and apparatus for acid pre-hydrolysis of biomass to hydrolyze hemicellulose to sugars. This and other objects of the invention will become clear from an inspection of the detailed description of the invention and from the appended claims.

DETAILED DESCRIPTION OF THE DRAWING

Figure 1A:
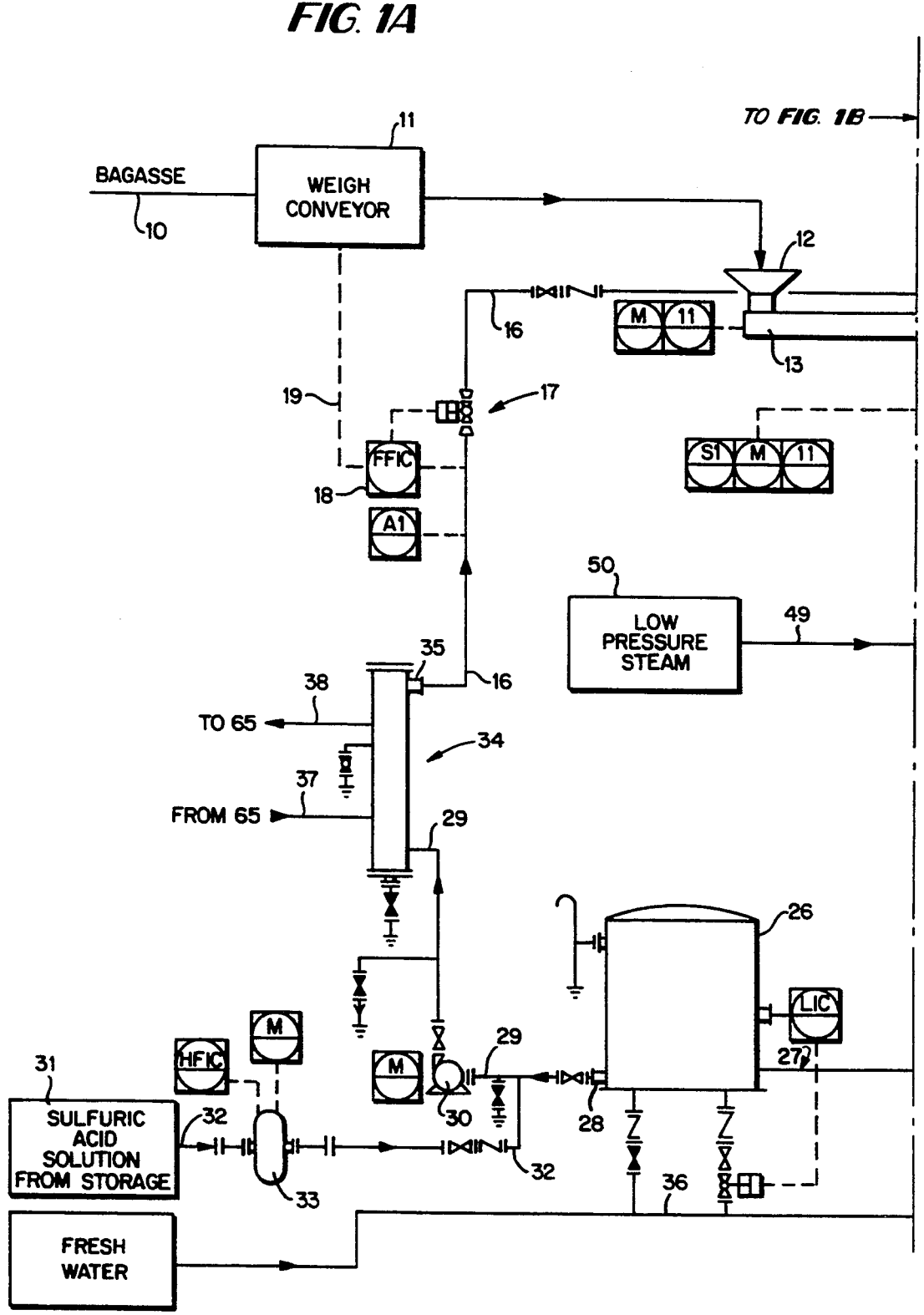
FIG. 1 is a flow sheet illustrating exemplary apparatus providing a reactor system according to the present invention, and for practicing the method of acid pre-hydrolysis according to the invention
Figure 1B:
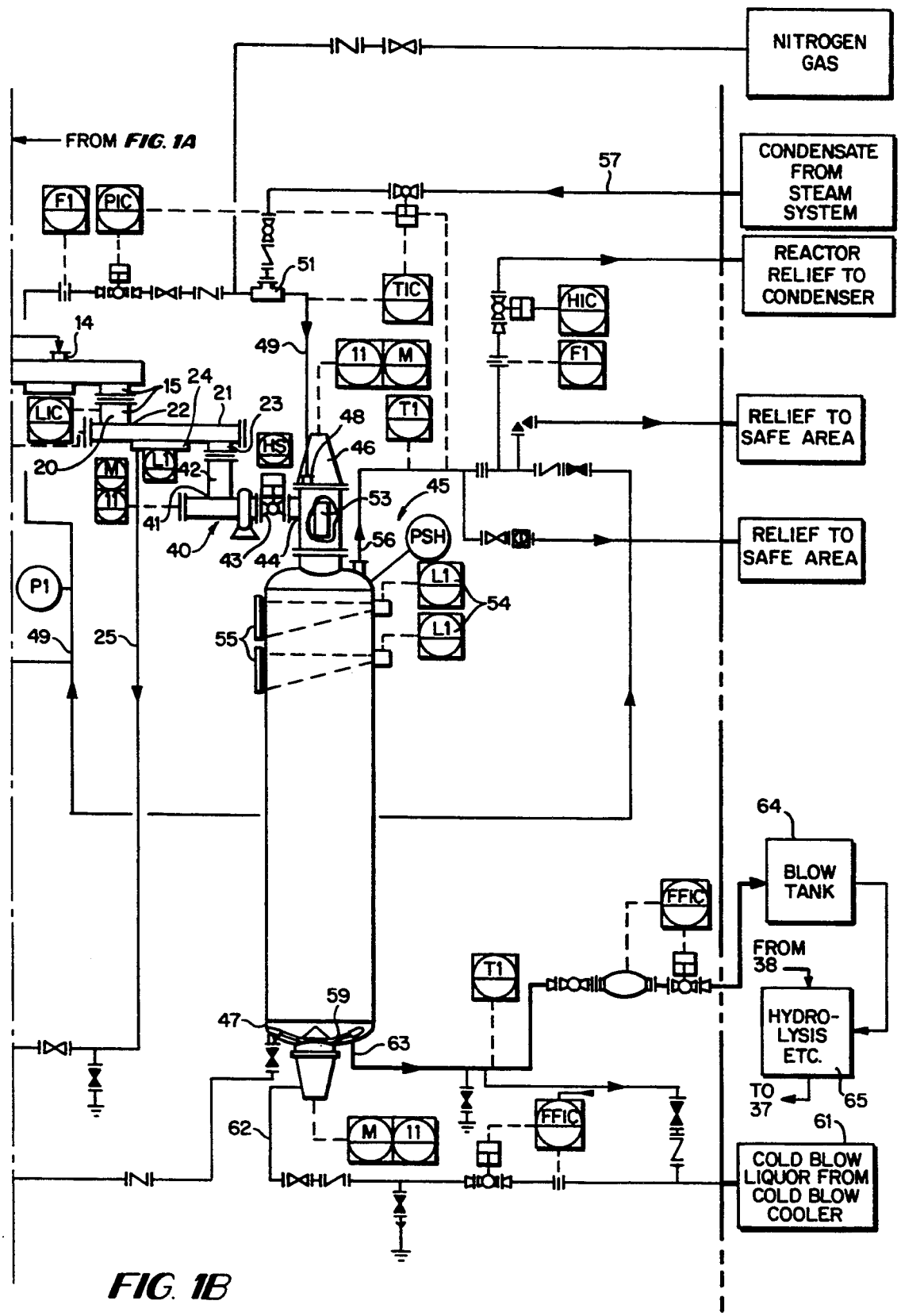

FIG. 1 schematically illustrates an exemplary reactor system according to the present invention. All of the individual components of the reactor system are themselves known per se, making the reactor simple and easy to construct in a cost-effective manner.

In the system of FIG. 1, bagasse, or other biomass, in line 10 is fed to a weigh conveyor 11, and then to the inlet 12 of an acid mixer 13. An acid solution inlet 14 also is provided to the acid mixer 13, and an outlet 15 is provided opposite the inlet 12. In the line 16 feeding acid solution to the inlet 14 a flow control valve 17 is provided. The amount of acid solution that is allowed to flow through the flow control valve 17 is controlled by the conventional controller 18 which receives a signal via input line 19 from the weigh conveyor, so that the amount of acid solution added to the mixer 13 is dependent upon the mass of the biomass fed to inlet 12.

The mineral acid added to the inlet 14 may be any suitable mineral acid, such as hydrochloric, sulfuric, or nitric acid, and typically is dilute, that is has a concentration of about 0.5–3.0%. It is also preferably heated to the neighborhood of about 130° to 150° F. in the manner that will be subsequently described. The amount of acid solution added is enough to form a slurry of biomass and solution in mixer 13 to ensure proper wetting of the biomass with mineral acid (e.g. forming a slurry of about 8 to 12% BD consistency, typically about 10%) while providing sufficient concentration of acid to eventually hydrolyze the hemicellulose in the biomass.

The mixer 13 can be, for example, a conventional Kamyr ® steam mixer.

The outlet 15 from the mixer 13 is connected by a vertical chute 20 to an impregnation press 21, vertically below it. The impregnation press 21 may be a FKC ™ screw press, having an inlet 22, a biomass outlet 23, and a pressate outlet 24. In the press 21, the slurry is dewatered so as to minimize the amount of steam required to heat the biomass to reaction temperature, and to maintain the desired sugar solution concentration after prehydrolysis. Typically the press 21 dewaters the biomass slurry to a consistency of about 35–50% (e.g. about 38% BD).

The pressate from the pressate outlet 24 passes in line 25 to a pressate tank 26 having an inlet 27, and an outlet 28. A line 29 connects the outlet 28 to a pump 30. Sulfuric, or other mineral acid, from source 31 passes in line 32 to an acid pump 33, which line 32 is in turn connected to the line 29 between the outlet 28 and the pump 30. The line 29 further extends to a pressate recycle indirect heater 34. In the heater 34, a hot fluid is passed in indirect, heat exchange, relationship with the pressate and added acid flowing therein, so that the acid solution in line 16 discharged from the outlet 35 of the heat exchanger 34 has an elevated temperature, e.g. roughly around 130° F.

The pressate in tank 26 will be diluted with fresh water mkae-up, added via line 36. The hot fluid that is used to heat the pressate/acid solution in heat exchanger 34 enters in line 37, e.g. at a temperature of about 180° F., and exits in line 38, e.g. at a temperature of about 147° F.

Vertically below the impregnation press 21 is a high density feed means 40, which preferably comprises a Kamyr ® K-5 thick stock pump, but may also comprise a feed screw or like device which is capable of bringing the biomass slurry up to reactor pressure and preventing blow back of acid vapors from the reactor to the impregnation press 21. The high density feed pump 40 has an inlet 41 which is connected to the outlet 23 from the press 21 by a vertical chute 42, and has an outlet 43 connected to a first inlet 44 of a vertical reactor 45. The vertical reactor 45 has a top 46, and a bottom 47, and is constructed so as to maintain a column of slurried biomass at superatmospheric pressure (e.g. about 40 psig) and a reaction temperature (e.g. at about 320° F.).

A second inlet 48 is also provided at the top 46 of the reaction vessel 45, this inlet 48 connected to a steam line 49 which is connected to a source of low pressure (e.g. 50 to 75 psig) steam 50. A de-superheating nozzle 51 preferably is provided in the line 49 just above the inlet 48. The steam added from line 49 directly contacts the biomass in a vapor phase at the top of the reactor 46 and heats it to reaction temperature, which, depending upon the particular biomass, acid, and the like, is about 250°–350° F., at a pressure of about 30–50 psig (preferably about 320° F. at a pressure of about 40 psig). An inert gas, such as nitrogen, should be added with the steam to provide a pad in the vapor space of reactor 45 (see FIG. 1B). Such addition will result in more stable temperature and pressure control.

Because of the high consistency of the biomass at the top 46 of the reactor 45, preferably a fluffer—shown schematically at 53—is provided in the top 46 of the reactor 45, for fluffing the high density (e.g. 35–40% consistency) biomass while steam is being added thereto.

The level of biomass within the reactor 45 may be sensed utilizing conventional gamma ray sources 54 and cooperating receptors 55. A safety vent 56 is provided for providing pressure relief to safe areas, and to provide relief for steam that is to pass to a condenser. Condensate from the steam system may be added in line 57 to the de-super heating nozzle 51.

At the bottom of the vertical reactor 45 is a rotating arm outlet device 59, such as a dilution discharge scraper. If the consistency of the bagasse or like biomass at the fluffer 53 is about 38% BD, then at the top of the reactor 45 but below the fluffer 53 the consistency will be about 34%, which will decrease to about 24% adjacent the bottom 47 of the reactor 45 due to steam addition and the like. In order to properly discharge the hydrolyzed biomass from the bottom 47 of the reactor 45, it is preferably diluted by the addition of fresh water or like cold blow liquor from source 61 through line 62. For example the cold blow liquor may be at a temperature of about 140° F., and a pressure about 85 psig. The hydrolyzed biomass is then cold blown from the reactor 45 through discharge line 63 to a blow tank 64 or the like. Ultimately, further hydrolysis processing takes place utilizing the conventional equipment illustrated only schematically at 65 in FIG. 1, but being, for example, apparatus such as described in U.S. Pat. Nos. 4,436,586 and 4,612,286. This treatment includes washing, and a sugar solution from the washing in the equipment 65 may be used as the heating fluid in line 37 for heat exchanger 34, while the sugar solution in line 38 is returned to the equipment 65.

Typically, the biomass is retained in the reactor 45 about 20 to 40 minutes, e.g. about 30 minutes. Of course the time will be sufficient, given the temperature and pressure conditions, the particular biomass, and the acid concentration and type, so that hydrolysis of hemicellulose to sugars takes place, but so that hydrolysis into cellulose does not.

It will thus be seen that according to the present invention a simple yet effective method and apparatus for acid pre-hydrolysis of biomass has been provided. The invention is useful with all types of biomass, not just bagasse, but other agricultural wastes, waste paper, and even municipal solid cellulose wastes. While the invention has been herein shown and described in what is presently conceived to be the most practical and preferred embodiment thereof it will be apparent to those of ordinary skill in the art that many modifications may be made thereof within the scope of the invention, which scope is to be accorded the broadest interpretation of the appended claims so as to encompass all equivalent methods and systems.

What is claimed is:

1. A single stage method of acid pre-hydrolysis of biomass, effecting hydrolysis of hemicellulose to five carbon sugars, comprising the steps of automatically, continuously and sequentially:
   (a) mixing biomass containing hemicellulose with a mineral acid solution of sufficient concentration to eventually hydrolyze the hemicellulose therein, and to form a slurry having a consistency that insures proper wetting of the biomass with mineral acid;
   (b) dewatering the slurry so as to minimize the amount of steam required to heat the biomass to reaction temperature and to maintain a desired sugar solution concentration after pre-hydrolysis;
   (c) heating the dewatered slurry to reaction temperature, at superatmospheric pressure by direct contact with steam; and
   (d) retaining the biomass in the dewatered slurry at reaction temperature and pressure conditions for a time sufficient to hydrolyze the hemicellulose of the biomass, but so that hydrolysis of cellulose does not occur, so that primarily five carbon sugars are produced.

2. A method as recited in claim 1 wherein step (a) is practiced by using biomass selected from the group consisting essentially of agricultural wastes, wastepaper, and municipal solid cellulose waste.

3. A method as recited in claim 1 wherein step (a) is practiced using municipal solid cellulose waste.

4. A method as recited in claim 1 wherein step (a) is practiced to form a slurry having a consistency of about 8–12%.

5. A method as recited in claim 1 wherein step (b) is practiced to dewater the slurry to a consistency of about 35–50%.

6. A method as recited in claim 5 comprising the further step (e), between steps (b) and (c), of fluffing the dewatered slurry.

7. A method as recited in claim 1 wherein step (b) is practiced to produce a pressate, and comprising the further steps of: (e) adding mineral acid to the pressate to form a mixture of pressate and acid, (f) heating the mixture of pressate and acid, and (g) using the heated mixture as the acid solution source in step (a).

8. A method as recited in claim 1 wherein steps (c) and (d) are practiced in a pressurized vertical reactor, and wherein step (c) takes place in a vapor phase at the top of the reactor, and comprising the further steps of diluting and cold blowing the biomass from the bottom of the reactor.

9. A method as recited in claim 1 wherein steps (c) and (d) are practiced at a pressure of about 40 psig, at a temperature of about 320° F., and for a time of about 30 minutes.

10. A method as recited in claim 9 wherein step (a) is practiced using bagasse, and an about 0.5–3.0% mineral acid solution.

11. A single stage method of acid pre-hydrolysis of biomass, effecting hydrolysis of hemicellulose to five carbon sugars, comprising the steps of automatically, continuously and sequentially:
   (a) mixing biomass containing hemicellulose with a mineral acid solution of about 0.5–3.0% to form a slurry having a consistency of about 8–12%;
   (b) dewatering the slurry to a consistency of about 35–50;
   (c) heating the dewatered slurry to a temperature of about 250°–350° F., at a pressure of about 30–50 psig, by direct contact with steam; and
   (d) retaining the biomass in the dewatered slurry at reaction temperature and pressure conditions for a time sufficient to hydrolyze the hemicellulose of the biomass, but so that hydrolysis of cellulose does not occur, so that primarily five carbon sugars are produced.

12. A method as recited in claim 11 wherein steps (c) and (d) are practiced at a pressure of about 40 psig, at a temperature of about 320° F., and for a time of about 30 minutes.

13. A method as recited in claim 11 wherein step (b) is practiced to produce a pressate, and comprising the further steps of: (e) adding mineral acid to the pressate to form a mixture of pressate and acid, (f) heating the mixture of pressate and acid, and (g) using the heated mixture as the acid solution source in step (a).

14. A method as recited in claim 11 comprising the further step (e), between steps (b) and (c), of fluffing the dewatered slurry.

15. A method as recited in claim 11 wherein steps (c) and (d) are practiced in a pressurized vertical reactor, and wherein step (c) takes place in a vapor phase at the top of the reactor, and comprising the further steps of diluting and cold blowing the biomass from the bottom of the reactor.

16. A method of acid pre-hydrolysis of biomass, effecting hydrolysis of hemicellulose to sugars, comprising the steps of automatically, continuously and sequentially:
   (a) mixing biomass containing hemicellulose with a mineral acid solution of sufficient concentration to eventually hydrolyze the hemicellulose therein, and to form a slurry having a consistency that insures proper wetting of the biomass with mineral acid;
   (b) dewatering the slurry to a consistency of about 35–50% so as to minimize the amount of steam required to heat the biomass to reaction temperature and to maintain a desired sugar solution concentration after pre-hydrolysis;
   (c) fluffing the dewatered slurry;
   (d) heating the dewatered slurry to reaction temperature, at superatmospheric pressure by direct contact with steam; and
   (e) retaining the biomass in the dewatered slurry at reaction temperature and pressure conditions for a time sufficient to hydrolyze the hemicellulose of the biomass.

17. A method of acid pre-hydrolysis of biomass, effecting hydrolysis of hemicellulose to sugars, comprising the steps of automatically, continuously and sequentially:
   (a) mixing biomass containing hemicellulose with a mineral acid solution of about 0.5–3.0% to form a slurry having a consistency of about 8–12%;
   (b) dewatering the slurry to a consistency of about 35–50%;
   (c) fluffing the dewatered slurry;
   (d) heating the dewatered slurry to a temperature of about 250°–350° F., at a pressure of about 30–50 psig, by direct contact with steam; and
   (e) retaining the biomass in the dewatered slurry at reaction temperature and pressure conditions for a time sufficient to hydrolyze the hemicellulose of the biomass.

18. A method of acid pre-hydrolysis of biomass, effecting hydrolysis of hemicellulose to sugars, comprising the steps of automatically, continuously and sequentially:
   (a) mixing biomass containing hemicellulose with a mineral acid solution of sufficient concentration to eventually hydrolyze the hemicellulose therein, and to form a slurry having a consistency that insures proper wetting of the biomass with mineral acid;
   (b) dewatering the slurry so as to minimize the amount of steam required to heat the biomass to reaction temperature and to maintain a desired sugar solution concentration after pre-hydrolysis;
   (c) heating the dewatered slurry to reaction temperature, at superatmospheric pressure by direct contact with steam;
   (d) retaining the biomass in the dewatered slurry at reaction temperature and pressure conditions for a time sufficient to hydrolyze the hemicellulose of the biomass;
   steps (c) and (d) being practiced in a pressurized vertical reactor; and step (c) taking place in a vapor phase at the top of the reactor; and
   (e) diluting and cold blowing the biomass from the bottom of the reactor.

19. A method as recited in claim 18 wherein steps (c) and (d) are practiced at a pressure of about 30–50 psig, and at a temperature of about 250°–350° F., and wherein step (d) is practiced for a time of about 20–40 minutes.

20. A method as recited in claim 18 wherein step (b) is practiced in a dewatering press, and comprising the further step of preventing vapors from the top of the reactor from passing back to the dewatering press.

21. A method as recited in claim 18 wherein the consistency of the biomass slurry at the top of the reactor is about 34%, and the consistency at the bottom is about 24%, and wherein said diluting step is practiced to dilute the biomass slurry to a consistency of about 8–12%.

22. A method as recited in claim 18 wherein said cold blowing takes place at a temperature of about 180° F.

23. A method of acid pre-hydrolysis of biomass, effecting hydrolysis of hemicellulose to sugars, comprising the steps of automatically, continuously and sequentially:
   (a) mixing biomass containing hemicellulose with a mineral acid solution of about 0.5–3.0% to form a slurry having a consistency of about 8–12;
   (b) dewatering the slurry to a consistency of about 35–50%;
   (c) heating the dewatered slurry to a temperature of about 250°–350° F., at a pressure of about 30–50 psig, by direct contact with steam;
   (d) retaining the biomass in the dewatered slurry at reaction temperature and pressure conditions for a time sufficient to hydrolyze the hemicellulose of the biomass;
   steps (c) and (d) being practiced in a pressurized vertical reactor; and step (c) taking place in a vapor phase at the top of the reactor; and
   (e) diluting and cold blowing the biomass from the bottom of the reactor.

24. A method as recited in claim 23 wherein the consistency of the biomass slurry at the top of the reactor is about 34%, and the consistency at the bottom is about 24%, and wherein said diluting step is practiced to dilute the biomass slurry to a consistency of about 8–12%.

25. A method of acid pre-hydrolysis of biomass, effecting hydrolysis of hemicellulose to sugars, comprising the steps of automatically, continuously and sequentially:
   (a) mixing biomass containing hemicellulose with a mineral acid solution of sufficient concentration to eventually hydrolyze the hemicellulose therein, and to form a slurry having a consistency that insures proper wetting of the biomass with mineral acid;
   (b) dewatering the slurry so as to minimize the amount of steam required to heat the biomass to reaction temperature and to maintain a desired sugar solution concentration after pre-hydrolysis;

(c) heating the dewatered slurry to reaction temperature, at superatmospheric pressure by direct contact with steam;

(d) retaining the biomass in the dewatered slurry at reaction temperature and pressure conditions for a time sufficient to hydrolyze the hemicellulose of the biomass;

(e) adding mineral acid to the pressate from step (b) to form a mixture of pressate and acid;

(f) heating the mixture of pressate and acid; and (g) using the heated mixture as the acid solution source in step (a).

26. A method as recited in claim 25 wherein step (f) is practiced by (g) washing the biomass from step (d) to produce a sugar solution having a temperature well above 100° F., and (h) passing the sugar solution into indirect, heat exchange, contact with the mixture of pressate and acid.

27. A method as recited in claim 26 comprising the further step (i) of automatically controlling the amount of acid solution added in step (a) in response to the mass flow rate of biomass used therein.

28. A method of acid pre-hydrolysis of biomass, effecting hydrolysis of hemicellulose to sugars, comprising the steps of automatically, continuously and sequentially:

(a) mixing biomass containing hemicellulose with a mineral acid solution of about 0.5-3.0% to form a slurry having a consistency of about 8-12%;

(b) dewatering the slurry to a consistency of about 35-50%, and to produce pressate;

(c) heating the dewatered slurry to a temperature of about 250°-350° F., at a pressure of about 30-50 psig, by direct contact with steam;

(d) retaining the biomass in the dewatered slurry at reaction temperature and pressure conditions for a time sufficient to hydrolyze the hemicellulose of the biomass;

(e) adding mineral acid to the pressate from step (b) to form a mixture of pressate and acid;

(f) heating the mixture of pressate and acid; and (g) using the heated mixture as the acid solution source in step (a).

29. A method as recited in claim 28 wherein step (f) is practiced by (g) washing the biomass from step (d) to produce a sugar solution having a temperature well above 100° F., and (h) passing the sugar solution into indirect, heat exchange, contact with the mixture of pressate and acid.

* * * * *